United States Patent [19]

Rounbehler et al.

[11] Patent Number: 5,268,302
[45] Date of Patent: Dec. 7, 1993

[54] SELECTIVE, HIGH SPEED DETECTION OF VAPORS WITH ANALYSIS OF MULTIPLE GC-SEPARATED PORTIONS

[75] Inventors: David P. Rounbehler, Bedford; David P. Lieb, Lexington, both of Mass.

[73] Assignee: Thermedics Inc., Woburn, Mass.

[21] Appl. No.: 35,541

[22] Filed: Mar. 22, 1993

Related U.S. Application Data

[63] Continuation of Ser. No. 592,425, Oct. 4, 1990, abandoned, which is a continuation-in-part of Ser. No. 529,813, May 29, 1990, abandoned.

[51] Int. Cl.$^5$ .................... G01N 30/08; G01N 1/18; G01N 30/88; G01N 33/94
[52] U.S. Cl. ........................ 436/96; 73/23.2; 73/23.41; 73/23.42; 422/88; 422/89; 422/91; 436/98; 436/107; 436/111; 436/157; 436/158; 436/161; 436/178; 436/816; 436/901
[58] Field of Search .............. 73/23.2, 23.41, 23.42; 422/88, 89, 91; 436/106, 107, 111, 157, 158, 161, 174, 178, 96, 98, 816, 901

[56] References Cited

U.S. PATENT DOCUMENTS

| | | | |
|---|---|---|---|
| 3,304,159 | 2/1967 | Hinsvark | 23/230 |
| 3,403,978 | 10/1968 | Favre | 23/230 |
| 3,430,482 | 3/1969 | Dravnieks et al. | 73/23.1 |
| 3,518,059 | 6/1970 | Levy | 23/232 |
| 3,589,171 | 6/1971 | Haley | 73/23.1 |
| 3,701,632 | 10/1972 | Lovelock | 23/232 E |
| 3,877,875 | 4/1975 | Jones | 23/230 |
| 3,925,022 | 12/1975 | Showalter et al. | 422/88 |
| 3,996,009 | 12/1976 | Fine et al. | 73/23.35 |
| 4,054,414 | 10/1977 | Grob et al. | 23/230 PC |
| 4,089,207 | 5/1978 | Patton | 73/23.25 |
| 4,159,894 | 7/1979 | Hu | 23/230 PC |
| 4,401,763 | 8/1983 | Itoh | 436/115 |
| 4,467,038 | 8/1984 | Scott | 436/115 |
| 4,509,855 | 4/1985 | Gay | 356/72 |
| 4,534,207 | 8/1985 | Szakasits et al. | 73/23.1 |
| 4,650,499 | 3/1987 | Scott | 55/18 |
| 4,701,306 | 10/1987 | Lawrence et al. | 422/88 |
| 4,778,764 | 10/1988 | Fine | 436/116 |
| 4,795,853 | 1/1989 | Miller et al. | 585/733 |
| 4,805,441 | 2/1989 | Sides et al. | 73/23.1 |
| 5,019,517 | 5/1991 | Coulson | 422/89 |
| 5,092,155 | 3/1992 | Rounbehler et al. | 436/156 |
| 5,092,156 | 3/1992 | Miskolczy | 436/156 |

FOREIGN PATENT DOCUMENTS

| | | |
|---|---|---|
| 1262529 | 2/1972 | United Kingdom . |
| WO83/01512 | 4/1983 | World Int. Prop. O. ............ 422/89 |

OTHER PUBLICATIONS

N. C. Sha et al. Chem. Abstr. 1977, 89:190513c.
W. Bertsch et al. Chem. Abstr. 1977, 89:151662f.
C. J. Thompson et al. Chem. Abstr. 1972, 80:28775g.
R. J. Pell et al. Chem. Abstr. 1987, 107:108507n.

Primary Examiner—James C. Housel
Assistant Examiner—Arlen Soderquist
Attorney, Agent, or Firm—Herbert Messenger

[57] ABSTRACT

A method and apparatus for selective, high speed detection of vapors of specific gas-chromatographically-separable compounds. In the disclosed method separate analyses are performed on two portions of a gas sample formed by flash-heating trapped vapors to successively higher temperatures while flowing hydrogen carrier gas over coatings in/on which the vapors are held. Within a total time interval of about twenty seconds 1) two sample portions are formed, 2) each portion is rapidly separated in two series-connected, high speed, temperature-programmed gas chromatographs, and 3) specific compounds are identified by detection of NO gas formed during an oxidative pyrolysis of each separated portion. One application of the described method and apparatus is the rapid, selective, and sensitive detection of nitrogen-containing compounds such as the drugs methamphetamine, cocaine, and heroin.

16 Claims, 6 Drawing Sheets

SELECTIVE, HIGH SPEED DETECTION OF VAPORS WITH ANALYSIS OF MULTIPLE GC-SEPARATED PORTIONS

CROSS-REFERENCE TO RELATED APPLICATIONS

This is a continuation of application Ser. No. 07/592,425 filed Oct. 4, 1990, now abandoned, which is a continuation-in-part of application Ser. No. 07/529,813 filed May 29, 1990, now abandoned.

BACKGROUND OF THE INVENTION

This invention relates to selective detection of vapors and more particularly to the high speed, highly sensitive and selective detection of specific gas-chromatographically-separable compounds, especially certain nitrogen-containing compounds such as methamphetamine, cocaine, and heroin.

Instruments are known which utilize gas chromatographs to separate constituents of a gas sample and then detect specific compounds among the separated constituents. For example, U.S. Pat. Nos. 4,778,764 and 4,843,016 to Fine, whose disclosures are incorporated herein by reference to those patents, describe an apparatus and method for detecting nitrogen-containing compounds in a sample by chromatographically separating constituents, heating the separated constituents in the presence of oxygen to convert bound nitrogen to nitric oxide (NO) gas, and then detecting the nitric oxide gas to determine the presence of the compounds. Apparatus employing similar basic concepts, which operates to separate then pyrolyze and detect nitrogen-containing compounds known as N-nitrosamines, is described in U.S. Pat. No. 4,301,114 (Rounbehler et al.) whose disclosure is also incorporated herein by reference to that patent.

In certain detection applications neither excluded from nor described in the above-referenced Fine patents, it is important that sample analyses be performed quickly and with high selectivity and sensitivity. For example, air samples containing vapors of explosives or drugs acquired from surfaces such as the clothing or luggage of person, or from containers, must be processed quickly and accurately by a detector for the instrument to be useful in screening personnel or articles passing in quantity through a checkpoint. High sensitivity is needed for detection of minute quantities of specific vapors which may be present in gas (e.g., air) samples acquired in relatively short time intervals. High selectivity is essential for accurate detection, particularly for avoiding false alarms which may be triggered if vapors from compounds not of interest Produce signals which are not clearly separable from those produced by compounds of interest. Selectivity can be difficult to achieve for "dirty" samples containing many compounds, particularly if time and/or equipment for clean-up of individual (or successive) samples are not available.

Accordingly, it is an object of the invention to provide an improved method and apparatus for detecting vapors of specific compounds separable by gas chromatography.

It is an object of the invention to provide a high speed, highly selective system and method for detecting vapors of specific gas-chromatographically (GC)-separable nitrogen-containing compounds.

It is a particular object of the invention to provide a high speed, highly selective method and apparatus for detecting vapors of drugs such as methamphetamine, cocaine, and heroin.

It is a particular object of the invention to provide a high speed, highly selective method and apparatus for detecting vapors of GC-separable compounds in which the vapors of at least one specific compound of interest have substantially higher volatility than the vapors of at least one other specific compound of interest.

It is a particular object of the invention to provide a method and apparatus which achieve the foregoing objectives without diverting a portion of each gas sample from passage through the second of two series-connected gas chromatographs.

SUMMARY OF THE INVENTION

The invention is an improved method and apparatus for rapid selective detection of vapors of specific gas-chromatographically-separable compounds. The detection system preferably includes two high speed, temperature-programmed gas chromatographs in series for providing a two-step separation of vapors of compounds to be detected such as the nitrogen-containing drugs methamphetamine, cocaine, and heroin, followed by a detector of the separated vapors. In certain embodiments a pyrolyzer is positioned downstream of the second gas chromatograph (GC2) for heating the separated vapors to produce a specific gas. The pyrolyzer leads to a detector whose detection of the specific gas at predetermined times generates signals indicating the presence and identity of the specific compounds.

Enhanced selectivity and accuracy of detection are provided by inclusion in the invention of operating steps and components according to which successive analyses are rapidly performed on two portions of a gas sample, either or both of which contain vapors of specific compounds of interest. Initially, vapors are focussed in a vapor concentrator which later serves, together with a carrier gas supply, to form and inject portions of a gas sample into the first gas chromatograph (GC1) of two series-connected temperature-programmed gas chromatographs. As a carrier gas such as hydrogen is passed through the vapor concentrator, the vapor concentrator is flash-heated for a brief interval such as one second to a temperature sufficient to desorb highly volatile materials, and then is very rapidly cooled. As a result an initial or first portion of a gas sample is formed and very rapidly directed into GC1 while less volatile vapors remain held within the vapor concentrator. With both gas chromatographs operating under initial parts of their preset temperature programming, GC-separable vapors included in the initial portion of the gas sample are rapidly and successively separated in GC1 and GC2. The separated vapors then very rapidly pass to the pyrolyzer and the detector for production and detection, respectively, of the specific gas of interest and identification of any specific compounds to be detected in the initial portion of the sample.

Preferably the temperature programs of GC1 and GC2 are such that immediately following the processing of the initial portion of the sample their temperatures are very rapidly increased to drive any remaining vapors from their GC coatings and thus provide clean GC's for effective separation of later portions of gas samples. Then, at a preselected time, typically less than about ten seconds following its initial flash-heating, and with carrier gas still flowing through the detection system, the vapor concentrator is again flash-heated or "fired" for a brief interval to a higher temperature than its initial firing. As a result vapors of all remaining specific compounds of interest are released (without decomposition) into flowing carrier gas to form a second portion of a gas sample which is very rapidly directed into GC1.

With continued temperature programming to enhance separation of vapors and then rapidly drive the separated vapors of the second portion of the sample vapors out of the gas chromatographs, GC1 and later GC2 effectively and cleanly separate the vapors to be detected from each other and from other constituents in the sample. The separated vapors in this second portion of the gas sample then very rapidly pass to the pyrolyzer and the detector for production and detection of the specific gas of interest. Immediate identification can be made of specific compounds to be detected in the second portion of the gas sample.

In a preferred detection system two series-connected vapor concentrators VC1 and VC2 are positioned ahead of the first gas chromatograph GC1 to permit rapid concentration of vapors. Concentration, GC injection, and separation of vapors are achieved at high speed by electrical circuitry which provides rapid, precise heating of VC1, VC2, GC1, and GC2. In association with a computer, the control circuit senses resistance of small diameter metal tubes of the vapor concentrators and gas chromatographs as voltage is applied and current is flowed through the tubes to heat vapors therein. At very closely-spaced intervals (e.g., 10 millisecond intervals) power input/tube current is adjusted to achieve desired tube resistances (hence tube temperatures) according to resistance values stored in the computer. In this way rapid, precise profiles of tube temperature with time are achieved to rapidly focus, move, and separate vapors included in gas samples.

Preferred uses of the invention are to detect, by analysis of vapors, one or more of the following drugs: methamphetamine (ice), cocaine, and heroin. The specific gas produced and detected in such uses is nitric oxide (NO) which is produced by pyrolysis of the drug vapors in the presence of oxygen, and may then be detected in an ozone-based chemiluminescence detector. Methamphetamine, if present, is detected in the initial portion of a gas sample since its vapors are relatively volatile, while cocaine and heroin are detected in the second portion of the sample. A typical time interval to complete the analysis of both portions of a sample is about twenty seconds, as measured from the initial flash-heating of the vapor concentrator.

DESCRIPTION OF THE PREFERRED EMBODIMENTS

The vapor detection system and method of the present invention is related in part to that disclosed in the U.S. patent application "Selective, High Speed Detection of Vapors With GC Bypass of Volatiles", Rounbehler et al., filed of even date herewith. According to the vapor detection system of that other application a valve is employed to divert an initial portion of the effluent of a first gas chromatograph (GC1) from passage through the second of two series-connected gas chromatographs (GC1 and GC2) so that highly volatile material in the initial portion cannot coat and overload critical surfaces of GC2. The system of the present invention operates without the bypass valve and passes an entire sample through its gas chromatographic column, preferably two series-connected GC's. However, it forms and analyzes the sample in two successive portions, the first containing highly volatile materials which may include one or more compounds to be detected (e.g., methamphetamine) and the second containing less volatile materials such as cocaine and heroin. Cleaning of the GC's by very rapidly increasing their temperatures removes any vapors remaining in their coatings after the time of detection of compounds in the first time interval so that clean GC's are available for effective separation of vapors in the second portion of the gas sample.

Figure 1:
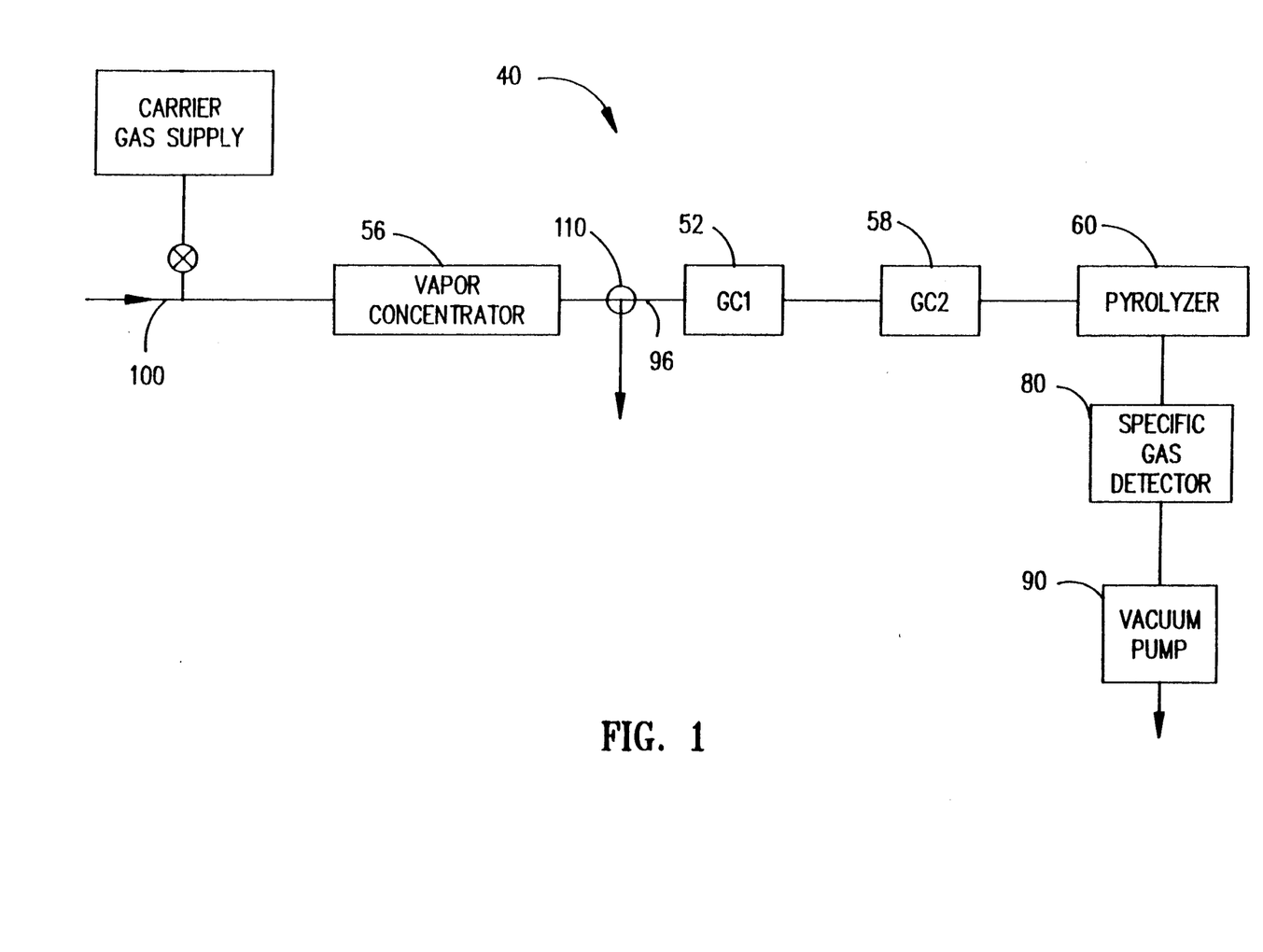
FIG. 1 is a block diagram of a vapor detection system of the invention illustrating certain basic components.
Figure 2:
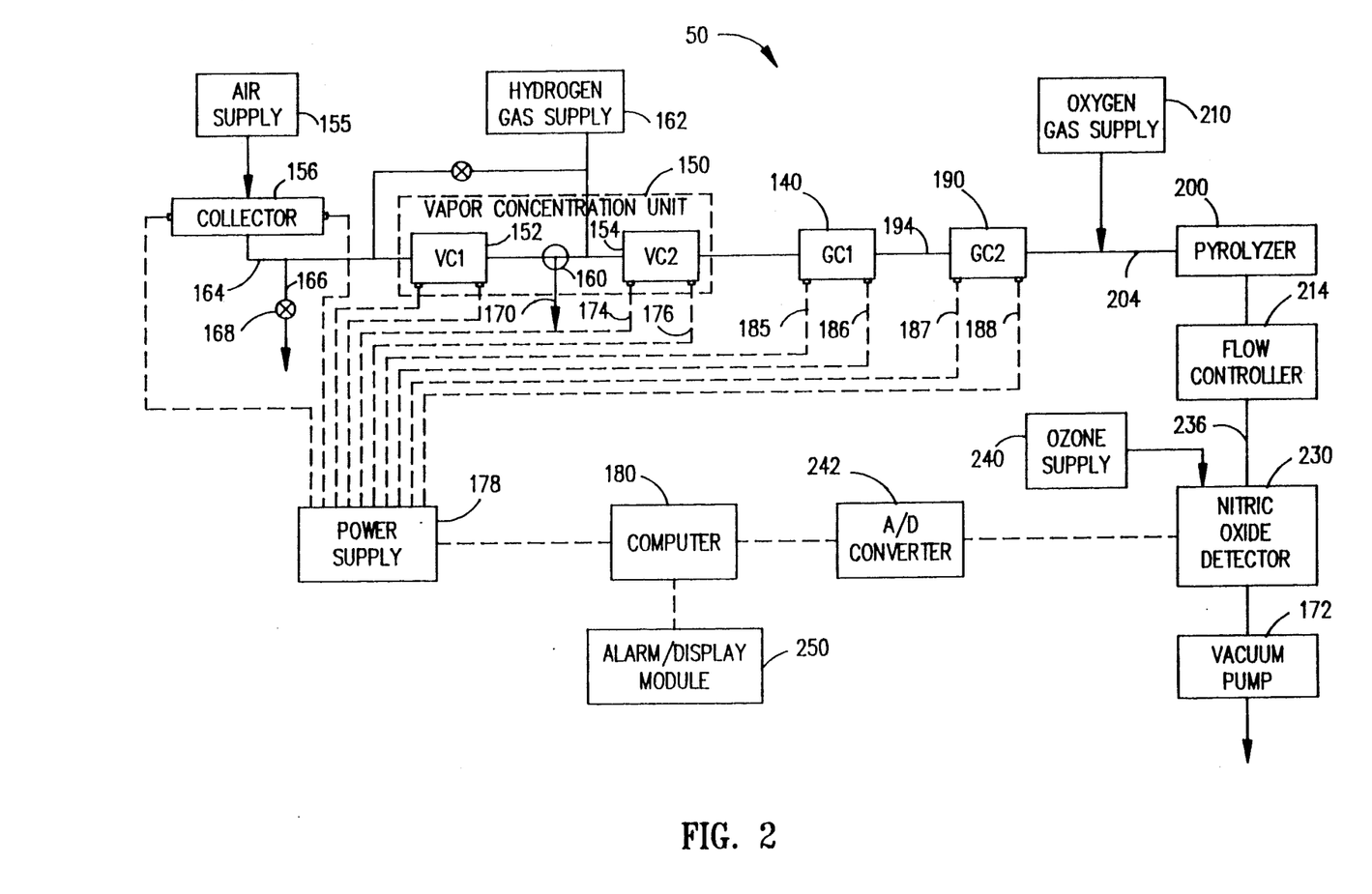
FIG. 2 is a block diagram of a vapor detection system according to a preferred embodiment of the invention

FIG. 1 is a block diagram illustrating a vapor detection system 40 and some of its principal components according to the invention. FIG. 2 shows in more detail a preferred system 50 for detecting vapors of certain nitrogen-containing compounds such as the drugs methamphetamine, cocaine, and heroin. The systems 40 and 50 rapidly detect vapors in gas samples by forming portions of gas samples in successive time intervals, chromatographically separating the vapors from one another, heating the separated vapors under conditions to form a specific gas such as nitric oxide (NO), and then detecting the specific gas at times which indicate the compounds of interest. A key aspect of these systems 40 and 50 and their operation is the temperature programming of certain components such as their vapor concentrators and gas chromatographs. Precise, rapid and very rapid heating of coatings in which vapors are trapped and separated permits provides high resolution of output signals and fast, accurate analyses of samples.

As used herein, the term "vapors" means materials not only in the gas phase but also in the form of aerosols and fine suspensions of particles. Such vapors may be present in ambient air in minute quantities (e.g., 0.1 parts explosives or drugs per trillion parts air or less) or readily stripped from surfaces and collected by passing air over the surface with or without heating and/or contacting the surface with air jets. The vapors of interest for detection according to the present invention are those which may be selectively retained and separated in high speed gas chromatographs. The term "gas sample" is used herein to refer a mixture of vapors and either air or another carrier gas (e.g., hydrogen or helium), and "air sample" refers to a mixture of vapors and air. The term "high speed" or "rapidly" generally refers to an action or event which occurs during a time interval of less than about 30 seconds and "very high speed" or "very rapidly" refers to an action or event which occurs during a time interval of less than about 2 seconds.

Detection of vapors according to the invention is first described with reference to FIG. 1 which shows in simplified form a system 40 for detecting vapors of specific compounds. A more detailed description of various components is provided below with reference to the system of FIG. 2

The vapor detection system 40 includes a first high speed gas chromatograph 52 (GC1 52) and a vapor concentrator 56 for trapping vapors and then later very rapidly directing portions of a gas sample into GC1 52. Downstream of GC1 52 is a second high speed gas chromatograph 58 (GC2 58), and both GC's typically include capillary tubing with thin, rapidly heatable coatings to selectively retain and separate vapors of specific compounds of interest from each other and from compounds not of interest. GC2 58 leads to a pyrolyzer 60 which is operable to heat vapors as they pass through the Pyrolyzer in a flow of carrier gas, with the heating performed at conditions such that a specific detectable gas is produced from vapors of the compound(s) of interest. The pyrolyzer 60 is connected to a specific gas detector 80 which includes or is in turn connected to a vacuum pump 90.

Although two series-connected GC's are shown in the systems of FIGS. 1 and 2, a single gas chromatograph—for example, of column length equal to the sum of the lengths of two separate GC columns—may be adequate to separate vapors of certain compounds to be detected according to the general principles of the invention. The use of two series-connected GC's is currently preferred for detection of methamphetamine, cocaine, and heroin because it affords more flexibility and ease of temperature programming and somewhat better resolution of signal peaks during operation. Also, although the systems illustrated herein each show a pyrolyzer and specific gas detector downstream of GC2, any other suitable detector of the compounds separated by the GC column(s)—e.g., a mass spectrometer—may be utilized in place of the pyrolyzer and specific gas detector provided its speed and sensitivity are sufficiently high for the desired application.

As is set forth in more detail in the detailed description of the vapor detection system 50 of FIG. 2, the vapor concentrator 56 may serve two functions. It operates not only to concentrate or focus vapors in a gas sample received along an inlet flow line 100 but also later to form and then very rapidly direct successive portions of a gas sample into the flow line 94 for passage to GC1 52. Preferably the vapor concentrator 56 includes, or is connected to, a multi-position valve 110 which may be set (1) to direct air and untrapped vapors along a vent line 120 to atmosphere during sample concentration or (2) (in a second position) to direct vapors in a flow of carrier gas to GC1 52 for further processing.

Operation of the system 40 will now be briefly described. First, a gas sample (e.g., air sample) is directed into the vapor concentrator 56 along the flow line 10. The air sample may, for example, be derived by air from a pressurized air supply connected to the flow line 100 through a collector (see FIG. 2) containing a metal coil coated with GC material on/in which vapors are initially trapped, but then released into the flowing air upon flash-heating of the coil. The collector may be a permanent part of the vapor detection system as in the walk-in booth disclosed in U.S. Pat. No. 4,909,089, or may be transportable from a portable vapor sampling probe as disclosed in U.S. Pat. No. 4,909,090. The disclosures of both of these patents (assigned to the assignee of the present invention) are incorporated herein by this reference to them.

As an air sample is passed through a tube of the vapor concentrator 56, vapors are trapped and concentrated in a coating on the inner tube surface (typical construction of a vapor concentrator is described below). Air and other materials not trapped within the vapor concentrator 56 are vented to atmosphere through the multi-position valve 110.

After vapors have been trapped and focussed in the vapor concentrator 56, the valve 94 is switched to a position permitting gas flow between the vapor concentrator 56 and GC1 52 along a flow line 96. Carrier gas such as hydrogen is then provided to the vapor concentrator 56 from a carrier gas supply 162 and its flow is maintained through GC1 52, GC2 58, the Pyrolyzer 60, specific gas detector 80, and the vacuum pump 90 during the remaining duration of the analysis of a sample.

With carrier gas flowing through the vapor concentrator 56, the vapor concentrator 56 is very rapidly heated (flash-heated), as in 0.05 seconds or less, to a predetermined temperature such as 125° C., held at temperature for a brief interval such as one second, then cooled, preferably very rapidly and to its initial temperature As a result an initial or first portion of a gas sample is formed from the carrier gas and highly volatile materials desorbed from the vapor concentrator 56, and this initial sample portion is very rapidly directed into GC1 52. Less volatile vapors remain held within the vapor concentrator 56.

At or soon after the flash-heating of the vapor concentrator 56, temperature programmed operation of both GC1 52 and GC2 58 commences, and temperatures of each GC at first are increased gradually during the time interval of analysis of the initial portion of the sample GC-separable vapors (e.g., methamphetamine) in the initial portion are rapidly separated in GC1 52, further separated in GC2 58, and then emerge and flow through the pyrolyzer 60. In passing through the pyrolyzer 60, the separated initial portion of the gas sample is heated under conditions such that vapors of specific compounds to be detected produce a specific, detectable gas. The gas may, for example, be nitric oxide produced from nitrogen-containing compounds such as methamphetamine heated in the presence of oxygen which is added to the effluent of GC2 58 (preferably upstream of the inlet of the pyrolyzer 60). Another specific gas such as $SO_2$ may be produced, depending on the vapors present and the reaction conditions provided in the pyrolyzer 60.

The gas produced at specific times (the pyrolyzer 60 preserves the separation achieved in the gas chromatograph 58) is passed to the detector 80 which as a consequence of detecting the specific gas generates signals from which the presence and identity of specific compounds may be determined.

The above-referenced formation and analysis of the initial portion of the gas sample typically is accomplished in a total time interval of about 5–10 seconds from the initiation of flash-heating of the vapor concentrator 56. Near the end of, or immediately following, this time interval the temperatures of GC1 52 and GC2 58 are very rapidly increased to drive any remaining vapors from their columns and hence provide clean coatings for effective separation of vapors in the second portion of the gas sample about to be formed and injected into GC1 52. Then, at a predetermined time such as about one second after the very rapid heating of GC1 52 and GC2 58, and with the GC's preferably held at their new higher temperatures, the vapor concentrator 56 is again flash-heated to desorb vapors into the flowing carrier gas and form the second portion of the gas sample which is very rapidly carried into GC1 52. This second "firing" of the vapor concentrator 56 is to a higher temperature (e.g., 250° C.) than the initial firing so as to desorb vapors of all remaining compounds to be detected, but the vapor concentrator 56 is, as in the initial firing, preferably very rapidly cooled after being held at the flash-heated temperature for about one second.

Processing and analysis of the second portion of the gas sample in the vapor detection system 40 then proceeds in a manner similar to that of the initial portion. However, in order that two successive GC-separations of the (less volatile) vapors in the second portion be rapidly completed in a short time interval (e.g. 5–10 seconds) GC1 52 and GC2 58 are maintained at relatively high temperatures and their programmed temperature schedules (temperature versus time profiles) preferably include ramplike portions (see FIGS. 5 and 6) to accelerate or drive separated vapors out of each gas chromatograph for subsequent pyrolysis and detection of specific gases.

FIG. 2 is a block diagram of a preferred system 50 for detecting vapors of nitrogen-containing compounds according to the invention, the system 50 being particularly useful in detecting drugs such as methamphetamine, cocaine and heroin. The diagram illustrates, in addition to the subsystems described with reference to FIG. 1, some additional components including controls and gas and power supplies.

As noted in the earlier discussion of the vapor detection system 40 of the invention, accurate detection may require that vapors be concentrated or focussed prior to injection of portions of a gas sample into the first gas chromatograph 140 (GC1 140) of the system 50. Accordingly, the vapor detection system 50 desirably includes (as a sample injector) a vapor concentration unit 150 which traps and concentrates vapors from a flow of air or hydrogen carrier gas passed through it, then later very rapidly release the concentrated vapors into a carrier gas for passage into downstream components. As illustrated in FIG. 2, the vapor concentration unit 150 comprises two vapor concentrators VC1 152 and VC2 154 connected by a flow line 158 in which a valve 160 is provided. Each of the vapor concentrators VC1 152 and VC2 154 is connected to a hydrogen gas supply 162 which supplies hydrogen to the concentrators as a carrier gas. A convenient method of Providing hydrogen for this purpose is to electrolyze water and collect and pressurize hydrogen liberated during electrolysis. Oxygen generated during the electrolysis may be used as a reactant in the high temperature pyrolyzer of the system 50. A Portion of the oxygen may also be ozonated in a conventional electric-powered ozonator to form ozone for use in an ozone-based nitric oxide detector of the vapor detection system.

The vapor concentration unit 150 is typically operated by first passing an air sample along an inlet flow line 164 into the VC1 152, as by directing air under pressure (e.g., 30 psi at a flow rate of 500 cm$^3$/min) from an air supply 155 through a metal coil of a collector 156 while flash-heating the coil (e.g., to 200° C.) to desorb vapors into a flow of air passed through the collector 156 without decomposing the vapors of interest. If the entire sample is not needed only a portion is directed into VC1 152 with the remainder vented through an exhaust line 166 containing a valve or other flow regulator 168. The effluent of VC1 152 (air and non-trapped constituents) is also vented through an exhaust line 170. The valve 160 is then switched to permit flow communication between the VC1 152 and the VC2 154 (typically of smaller internal volume). Vapors are then removed from the VC1 152 on which sample vapors are held, while flowing a carrier gas (e.g., hydrogen) from the supply 162 over the trapping surface. The vapors are carried into the VC2 154 where they are trapped and thus further concentrated and focussed.

Preferred vapor concentrators of the detection system 50 each include a small diameter tube such as, in the case of VC2 154, a 0.25 mm or 0.32 mm ID quartz capillary GC tube about 5 inches in length and whose inner surface has a thin coating (e.g., 1–3 microns) of a gas chromatographic material such as polymerized silicone (e.g, DB5 available from J&W Scientific of Folsom, Calif.) In effect, each concentrator is a short gas chromatograph tube. The Capillary tube is threaded through, or tightly encased in, a needlestock metal (e.g., stainless steel) tube whose outer surface is in contact with a cooled mass. This mass—e.g., a block of metal in thermal contact with a cooler such as a thermoelectric cooler (a well known electric-powered cooling device without moving parts) but electrically insulated from the metal tube by one or more layers of insulation such as silicone rubber wrapped around the metal tube—normally maintains the metal tube, and hence inner capillary tube, of the vapor concentrator 154 at or below room temperature (e.g., at a temperature such as about 10° C.) so that the GC coating will trap vapors from gas samples directed through the capillary tube. The outer metal tube is also connected, as by electrical lines 174 and 176, to a source of electric power such as power supply 178 which may include rechargeable batteries for controlled, extremely rapid resistance heating of the metal tube—for example, from about 10° C. to 250° C. in several milliseconds or less. This extremely rapid heating is preferably accomplished automatically under programmed control of a computer 180 and during which resistance of the metal tube is continually monitored and employed as a feedback parameter in controlling the power applied to the tube and hence the temperatures attained. A Preferred heating control is described below. Heating of the outer metal tube of the VC2 154 in turn heats the GC coating within the capillary tube to release or flash the vapors into a flow of carrier gas directed through the capillary tube.

Preferred carrier gases for use in the vapor detection system 50 are those which are pure, lightweight, and non-reactive with the compounds to be detected or with their thermal decomposition products or with other compounds which are likely to present in gas samples. Hydrogen, derived from electrolysis of water and furnished under Pressure to the vapor concentrator 154 from the carrier gas supply 162, has been found effective as a carrier gas for use in analysis of nitrogen-containing compounds such as explosives or drugs. It can be safely employed even when used in a system having a chemiluminescence-based NO detector supplied with ozone as one reactant, provided the amounts flowing through the NO detector are relatively small (as desired in a high speed system) and the NO detector is operated at low pressures (e.g., 1–20 torr). Helium is also suitable as a carrier gas, though less preferred.

After the vapors have been transferred to and trapped within the VC2 154, VC2 154 is flash-heated to successively produce an initial, and then a second, portion of a gas sample as described earlier with reference to the vapor concentrator 56. These portions are injected into a GC1 140, separated in GC1 140 and in a GC2 190 connected in series with GC1 140, and then further processed in a pyrolyzer 200 and a nitric oxide detector 230 as detailed below.

Both GC1 140 and GC2 190 selectively retain and separate vapors of specific compounds from other compounds to be detected and from compounds not of interest. These gas chromatographs, connected by a flow line 194, may have a construction similar to that of the vapor concentrator 154 except they are typically coiled, are substantially longer, and are held within an oven (not shown) and not in contact with a thermoelectric cooler (which may, however, also be housed within the oven). A typical length for each of GC1 140 and GC2 190 is about four feet. GC1 140 and GC2 190 are preferably maintained at temperatures somewhat higher (e.g., at 80° to 120° C.) than the vapor concentrators 152 and 154 by an oven or two separate ovens, except during analysis of a gas sample, particularly the second portion, when the temperatures of GC1 140 and GC2 190 are increased by application of electrical power along electrical lines 185, 186, 187, and 188 from the power supply 178 to the metal tubes encasing their GC capillary columns (with resistance feedback similar to that of VC1 152 and VC2 154 to help achieve precise temperature control and rapid and very rapid heating).

One or more blowers or fans (not shown) may also be included in the vapor detector system 50 to circulate air over components at selected times—for example, a blower within the oven enclosing GC1 140 and GC2 190 and operated when the GC's are not being rapidly heated so as to maintain the GC's at a uniform base temperature of about 95° C. Another blower may also be provided outside the oven and operated for a few seconds following the rapid heating of the metal tubes of GC1 140 and GC2 190 to circulate ambient air along a duct (extending from the blower to an opening in the oven wall) and over the metal tubes so as to hasten their cooldown.

Suitable vapor concentrators for use as VC1 152 and VC2 154 and gas chromatographs for use as GC1 140 and GC2 190 are contained within a Chemistry Module for a SENTOR portable drug detector available from Thermedics Inc. of Woburn, Mass.

Decomposition of vapors of compounds of interest is accomplished in the pyrolyzer 200 of the vapor detection system 50 which is connected by a flow line 204 to the outlet of GC2 190 so as to receive and heat vapors contained in the effluent of GC2 190. The gas sample entering the pyrolyzer 200 also contains oxygen furnished by an oxygen gas supply 210 and fed to the flow line 204 to mix with the vapors and carrier gas, the oxygen desirably being produced from electrolysis of water carried as a consumable material in a suitable reservoir (not shown) of the vapor detection system 50.

The high temperature pyrolyzer 200 includes a tube of small inner diameter (e.g., about 1.0 mm (0.04 inches) ID) and about 1.6 mm (0.06 inches) OD and is preferably formed of a high temperature nickel-base alloy such as Inconel 600. The working length of the tube (e.g., three inches) is surrounded by an electrical resistance heater which maintains the pyrolyzer tube at a preselected temperature such as about 750° C.–850° C. Nickel-containing materials have been found to be effective in promoting the reaction of cocaine and heroin vapors with oxygen to produce nitric oxide (NO) gas at a temperature of about 800° C. and a flow rate through the pyrolyzer 200 of about 60 cm$^3$/minute. Since small diameter pyrolyzer tubes of low temperature nickel-containing alloys may become brittle when operated at elevated temperatures, high temperature nickel alloys are preferred.

It has been found that for proper operation of the Pyrolyzer 200 an excess of oxygen is required. Since the hydrogen carrier gas will combine with oxygen to form water vapor upon mixing of these constituents, the flow of oxygen from the supply 210 is regulated to provide considerably more oxygen than needed to convert all the hydrogen in the gas sample entering the pyrolyzer 200. A typical volume ratio of oxygen to hydrogen is about 5:1.

The nickel of the pyrolyzer 200 is believed to act as a catalyst in the production of NO gas from vapors such as cocaine and heroin. Oxygen likely oxidizes nickel in the tube; then at elevated temperature nitrogen in the cocaine or heroin reduces the nickel oxide to form nickel and NO gas is produced. As a final step excess oxygen in the gas sample re-oxidizes the nickel tube surface to again form nickel oxide.

As is illustrated in FIG. 2, the high temperature pyrolyzer 200 is connected through a flow controller 214 and a nitric oxide detector 230 to the vacuum pump 172. The flow controller 214, which for example is a flow resistance element such as a twelve-inch section of coiled tube of the same material and size as employed in the pyrolyzer 200, may be needed to apply back pressure to the high temperature pyrolyzer 200. Raising the pressure level in the pyrolyzer 200 to, for example, 20–30 torr as contrasted with the very low pressure (e.g., 1–3 torr) maintained in the nitric oxide detector 230 may enhance the production of nitric oxide gas in the pyrolyzer 200 and improve sensitivity of detection. As an alternative to the flow controller 214, the pyrolyzer 200 may be lengthened or operated at somewhat higher temperature.

The nitric oxide detector 230 downstream of the two-position valve 220 operates to very rapidly detect nitric oxide gas in a gas sample passed through the detector 230 enroute to the vacuum pump 172. A preferred nitric oxide detector 230 is an ozone-based chemiluminescence detector of very high sensitivity-e.g., detection levels of up to about 1–100 picograms ($10^{-12}$–$10^{-10}$ g.) of NO-and speed and which operates on the basic set forth in U.S. Pat. No. 3,996,002 whose disclosure is incorporated herein by this reference to that patent. The detector 230 includes a reaction chamber to which a gas sample is fed along a flow line 236 and in which nitric oxide in the gas sample reacts with ozone furnished from an ozone gas supply 240. (The ozone supply 240 may include an ozonator in which oxygen from oxygen gas supply 210 is converted to ozone). Reaction of the ozone and nitric oxide yields an excited form of $NO_2$ whose decay to $NO_2$ yields radiation detectable by a photodetector or photondetector. Signals produced as a result of radiation are provided to an analog-to-digital (A/D) converter 242 connected to the computer 180. The computer 180 is in turn connected to an alarm/display module 250 which activates lights or other alarms if a specific signal is obtained, and also generates records or charts of signal amplitude versus time (chromatograms). Specific compounds of interest such as cocaine and heroin are identified and detected based on the occurrence of signal peaks during "detection windows" or times established through calibration runs in which test samples known to contain these compounds are analyzed in the vapor detection system 50.

Figure 11:
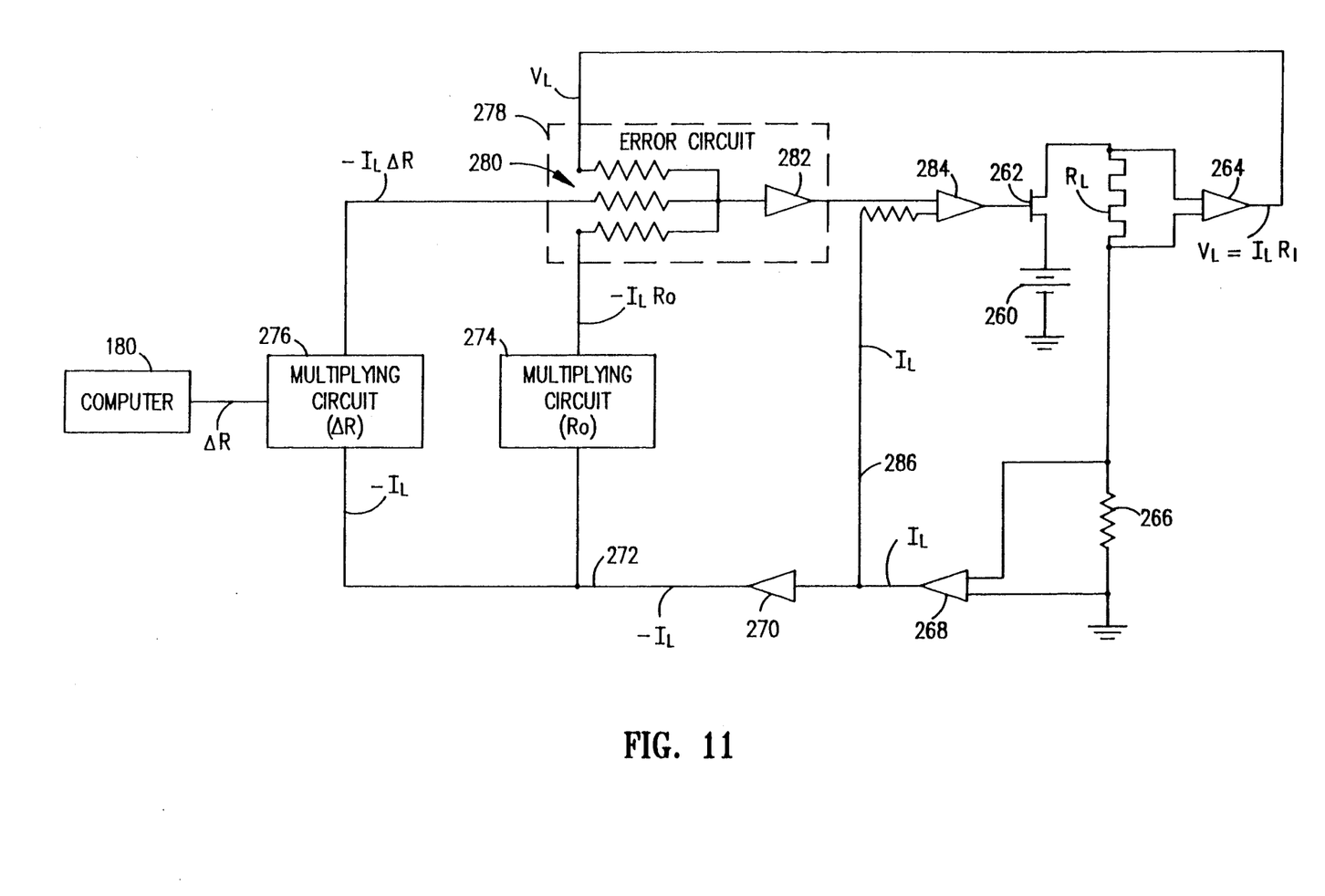
FIG. 11 is a schematic diagram of an electrical circuit for rapid, precise control of temperature, as in certain vapor concentrators and gas chromatographs of a vapor detection system of the invention.

A feature of preferred systems of the invention resides in the manner in which their vapor concentrator(s) and gas chromatograph(s) are heated to precise temperatures as indicated above. FIG. 11 shows a schematic circuit diagram of such an arrangement.

In this arrangement, and with reference to the system 50 of FIG. 2 by way of example, heating is supplied by passing current through the metal (e g., stainless steel) tubes forming the outer casings for the concentrators VC1 152 and VC2 154 and GC1 140 and GC2 190. As is well known, such metals increase in resistance with temperature To set each of VC1 152, VC2 154, GC1 140, and GC2 190 at a desired temperature, current is supplied at one end of its tube to flow through the length of the tube to the other end, which heats the tube and increases its resistance. The resistance is sensed from the current and voltage and compared with the known resistance corresponding to the desired temperature. Stored in the computer 180 for each value of temperature is a known value of resistance of the tube of VC1 152, VC2 154, GC1 140 and GC2 190, which may be determined by measurement or computation. For convenience, the stored resistance value may be the computed change in resistance from a base value $R_o$ determined at a base temperature, such as room temperature or 10° C., for example. Each time a change in temperature is desired, the circuit changes the current to adjust the tube resistance to the value of resistance corresponding to the desired temperature at that instant. The system thereby permits profiling the variation of the tube temperature with time in any desired manner by programming into the computer 180 the timed sequence of resistances to be obtained (e.g., resistance values at 10 millisecond intervals). This is accomplished by the circuit of FIG. 11.

In FIG. 11 the tube resistance is represented by load $R_L$, Current, as from power supplied by a battery 260, is passed through load $R_L$ under control of a power transistor (e.g. FET) 262. The voltage across $R_L$ is passed through an amplifier 264, whose output represents that voltage $V_L$, which equals $R_L \times I_L$, where $I_L$ is the load current. A small value (e.g. 0.1 ohm) resistor 266 is in series with load $R_L$. The voltage across resistor 266 represents the value of current $I_L$ and is supplied to an amplifier 268 whose output is representative of the load current $I_L$. The $I_L$ signal is inverted by an inverter 270 to provide on lead 272 a signal representative of $-I_L$. That signal is passed through a gain or multiplier circuit 274 to provide an output representing $-I_L \times R_o$ where $R_o$ is the fixed base resistance of the load (i.e., tube), as at room temperature.

The $-I_L$ signal from inverter 270 is also supplied to a multiplying circuit 276 (e.g. a multiplying DAC) which also receives a signal $\Delta R$ from computer 180. Signal $\Delta R$ represents the increment of resistance (over the base resistance $R_o$) for the load tube when it has attained the desired temperature, at the moment the $\Delta R$ signal is received by circuit 276. As indicated above, the computer 180 periodically (e.g, every 0.01 seconds) determines what $\Delta R$ is needed at that moment to correspond to the desired temperature.

The multiplying circuit 276 thus provides an output representing $-I_L \times \Delta R$. This output is summed with the $V_L$ signal from amplifier 264 and the $-I_L \times R$ signal from circuit 274 in an error circuit 278 comprising a summing network 280 and an error amplifier 282, whose error signal output represents $V_L - I_L(R_o + \Delta R)$. To make $R_L = R_o + \Delta R$, the output of error amplifier 282 is fed through an amplifier 284 to control transistor 262 to change $I_L$ by the amount required for the current heating effect on the load tube $R_L$ to change the tube resistance by the necessary amount to cause the error signal output from error amplifier 282 to become zero; i.e., $R_L$ then equals $R_o + \Delta R$. The gain of the loop containing amplifiers 282, 284 and 264 is made very high and may be of the order of one million An $I_L$ signal from amplifier 268 is applied over lead 286 to an input to amplifier 284 so that power transistor 262 will maintain current $I_L$ even for zero error signal (to maintain resistance sensing even when a change in heating power is not required).

In this way, the system specifies the tube resistance $R_L = R_o + \Delta R$ for the desired tube temperature, and adjusts the current flowing along the tube to heat the tube to attain the resistance, at which time the temperature is as desired. With the small mass of the tube, this arrangement permits extremely accurate and rapid creation of tube temperature, which may be varied precisely according to a desired time profile such as that of VC2 154 in FIG. 4 and that of GC1 140 and GC2 190 in FIGS. 5 and 6, respectively, as described below. For reduction of temperature, transistor 262 shuts off current, and the tube may cool naturally or under the influence of air blown over the tube. It will be understood that this resistance-determined arrangement may be used whenever rapid and precise temperature control is desired.

Figure 3:
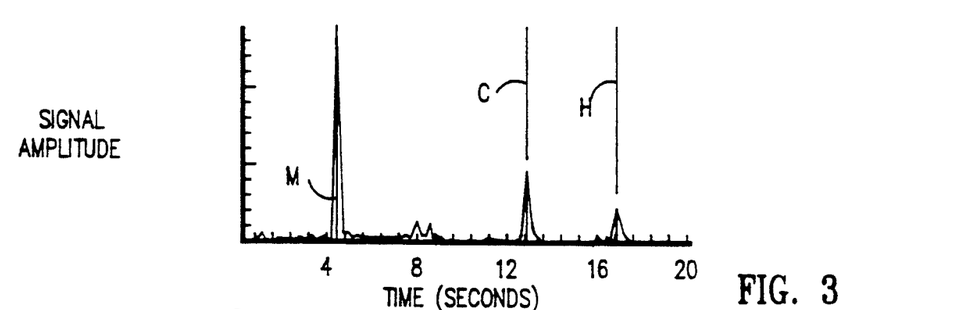
FIG. 3 is a chromatogram of NO signal amplitude versus time illustrating data for a gas sample formed from standard quantities of known drugs and evaluated in accordance with a preferred vapor detection system and method of the invention.

FIG. 3 is a plot of signal amplitude versus time (chromatogram) from tests of a gas sample formed from standard solutions of the drugs methamphetamine, cocaine, and heroin and analyzed according to the vapor detection system and method of the present invention. The vapors were formed by applying by syringe to a metal collector coil (as disclosed in U.S. Pat. No. 4,909,090) a microliter of solution of methanol and 50 picomoles each of methamphetamine, cocaine, and heroin, then flash-heating the collector while air was flowed through the collector and a vapor concentrator VC1 152 of a vapor detection system similar to that illustrated in FIG. 2. The signals of FIG. 3 are the output of an ozone-based chemiluminescence nitric oxide detector receiving the effluent of a pyrolyzer 200 which included a tube of Inconel 600 operated at about 800° C.

In FIG. 3 the vertical lines labeled M, C, and H correspond to the precalibrated times of detection for methamphetamine, cocaine, and heroin, respectively. The short horizontal line crossing each vertical line near the time axis denotes the detection "window" for the compound of interest. That is, any signal peak of sufficient size (e.g., peak height, mid-peak width, etc.) which is sensed within the detection window for a specific compound (e.g., cocaine) is considered as indicating the presence of that compound. According to such criteria the signals of FIG. 3 illustrate detection of all three of the drug standards, with methamphetamine being detected first, followed later by the detection of cocaine, and then heroin.

Figure 4:
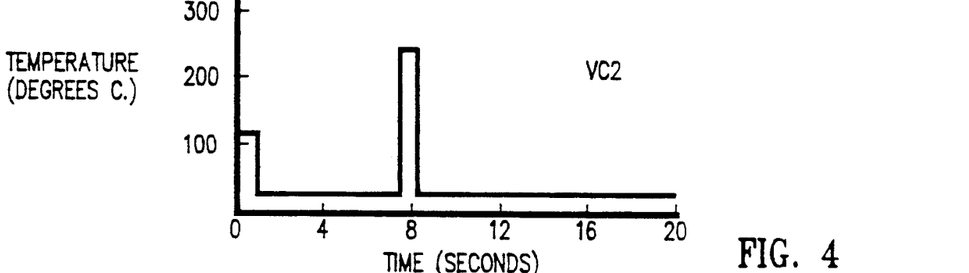
FIGS. 4–6 are plots of temperature versus time for the vapor concentrator, first gas chromatograph, and second gas chromatograph, respectively, as operated to produce the chromatogram of FIG. 3.
Figure 5:
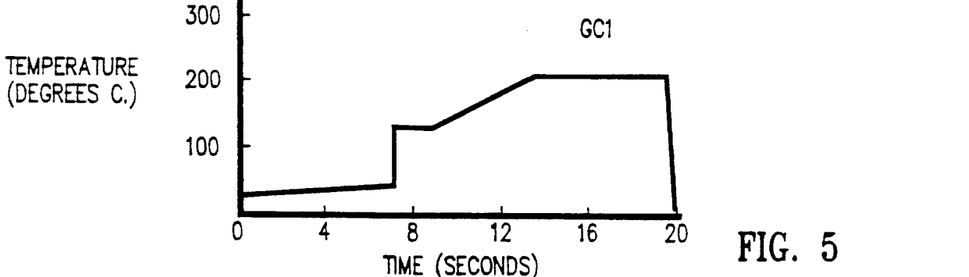
Figure 6:
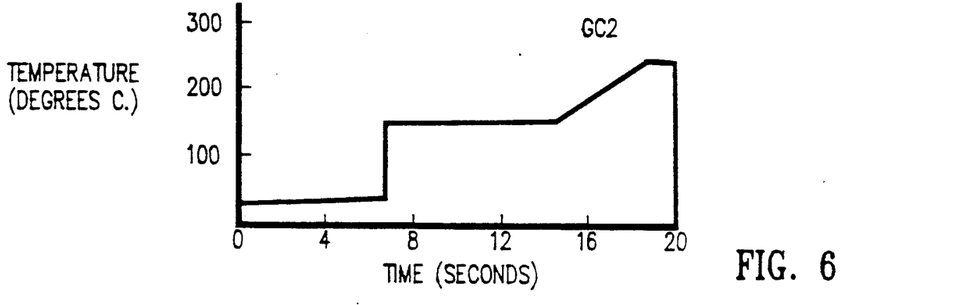
Figure 7:
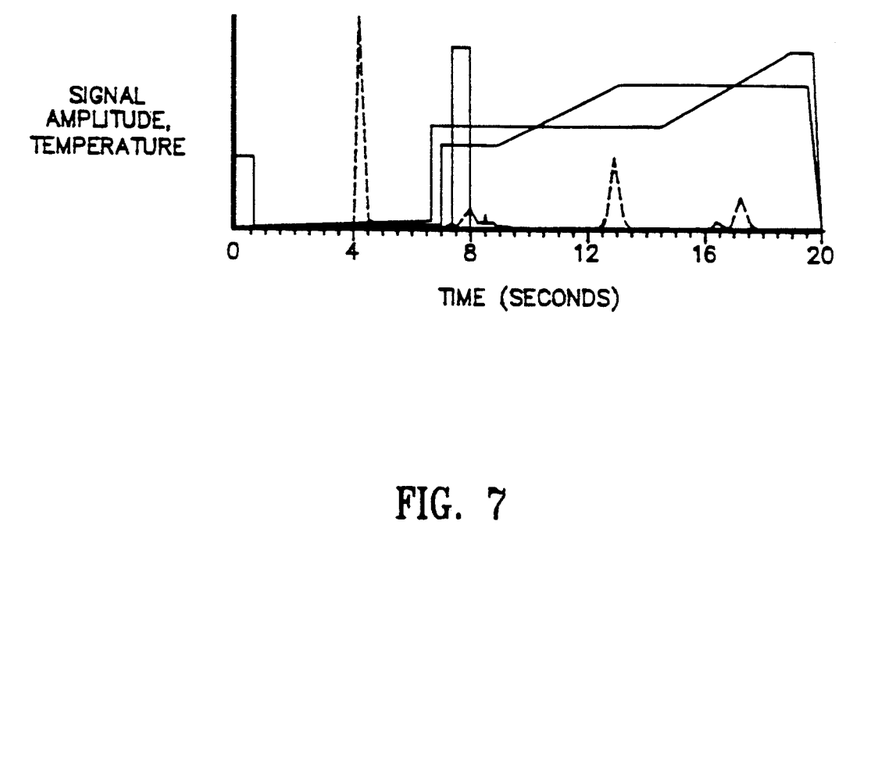
FIG. 7 is a composite plot versus time of the NO signals of FIG. 3 and the temperatures of FIGS. 4–6.

Temperature profiles employed for VC2 154, GC1 140, and GC2 190 during the FIG. 3 test of drug standards are shown in FIGS. 4, 5, and 6, respectively, and FIG. 7 shows a composite of these profiles and the output signals of the vapor detection system. The VC2 temperature schedule of FIG. 4 clearly shows its two firings (followed by very rapid coolings) for a duration of about 0.7 seconds each—first to a temperature of about 115° C. and then (at about t=8 seconds) a second firing to a temperature of about 245° C. These two firings correspond to the formation of the first and second portions of the gas sample, and it is evident from FIGS. 3 and 7 that methamphetamine is detected in the first, or highly volatile portion of the sample and cocaine and heroin are detected in the second portion.

The GC1 and GC2 temperature schedules (FIGS. 4 and 5) indicate a gradual increase of temperature of each gas chromatograph during the period of formation and analysis of the first portion of the gas sample, followed by very rapid increases in their temperatures (of about 90°–120° C. within 0.05 seconds) about 7 seconds following the first flash-heating of VC2. The temperature of each GC was then held at the flash-heated level for an additional time interval, then each temperature was ramped up to a higher level over a period of about four seconds and again held at this peak level.

With reference to FIG. 7, which is a composite of the temperature profiles of VC2 154, GC1 140, and GC2 190, and also shows the output signals of the tested drug standards, the GC1 and GC2 are rapidly fired prior to the second firing of VC2 to help clean the coatings of the gas chromatographs and to raise the temperatures of the GC's to levels at which the second portion of a gas sample can be rapidly and effectively separated in the GC's. After VC2 is fired for a second time to form the second portion of the gas sample and inject it into the first gas chromatograph, the temperature of GC1 is briefly held constant, then is ramped up to help drive vapors out of GC1 and into GC2. A similar temperature ramp is later applied to GC2, and formation and analysis of both portions of the gas sample are completed in about twenty seconds after the initial firing of VC2.

Figure 8:
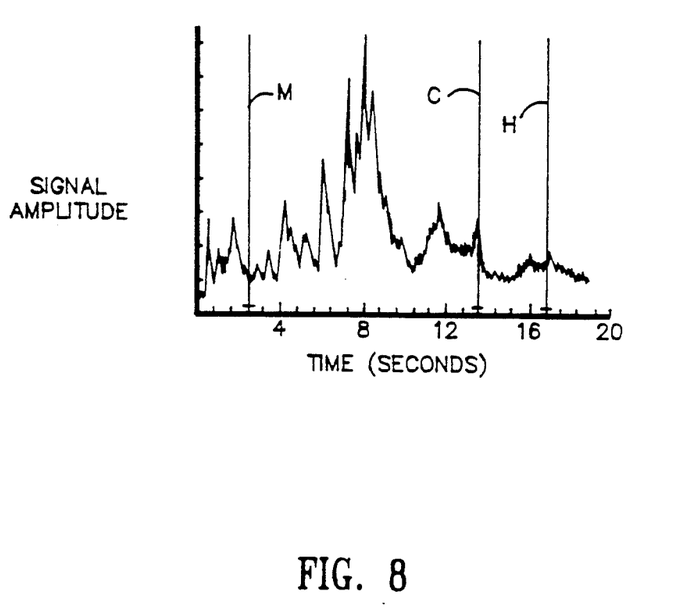
FIG. 8–10 are chromatograms of NO signal amplitude versus time illustrating test data for gas samples evaluated in accordance with a preferred vapor detection system and method of the invention.
Figure 9:
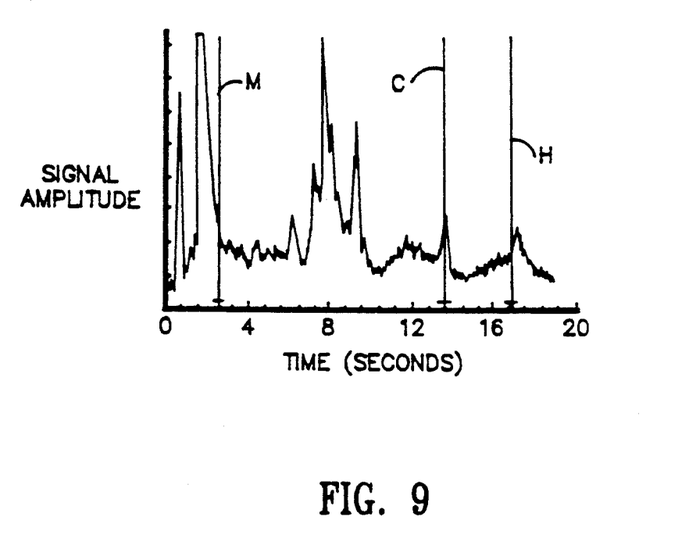
Figure 10:
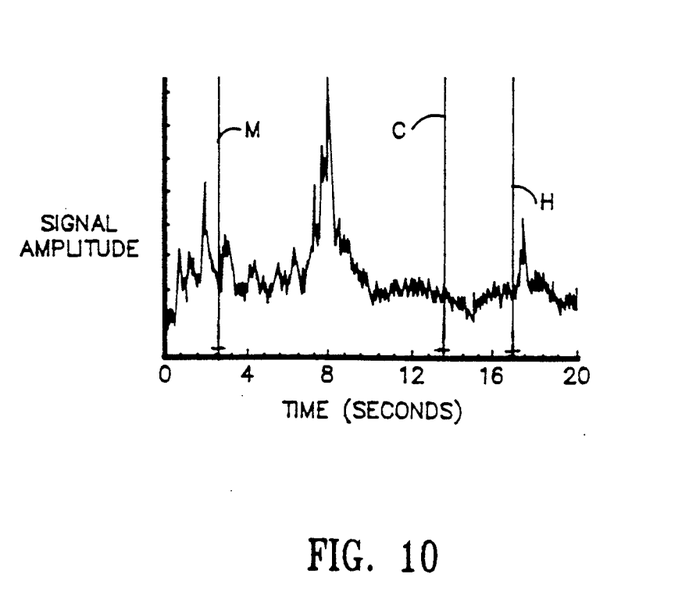

FIGS. 8, 9, and 10 are chromatograms from tests of samples collected using a portable sampling probe as described in the above-referenced U.S. Pat. No. 4,909,090 and whose metal coil collector was then transferred to a vapor detection system for processing in a system and manner as described with reference to FIGS. 2–7. FIG. 8 shows results of a test conducted on vapors acquired from the vicinity of a crack pipe, indicating a positive response for cocaine. FIG. 9 illustrates a positive response for cocaine for a sample acquired from the pants pocket of a person who had been handling crack. FIG. 10 shows a negative (no cocaine detection) response from a sample acquired from an unknown white powder, which lab tests using standard procedures (but lengthy as compared to the method of the present invention) later confirmed not be cocaine.

The above-described embodiments are intended as illustrative and non-limiting, and other embodiments may readily be apparent. The invention is defined by the claims which follow and includes all embodiments and their equivalents within the scope of the claims.

What is claimed is:

1. A method of rapidly and selectively detecting first and second specific compounds in a gas sample, said compounds being separable by gas chromatography and said first compound having a volatility substantially higher than the volatility of said second compound, comprising:

trapping vapors of said specific compounds in a vapor concentrator;

and while flowing a carrier gas through the vapor concentrator, forming and analyzing a first portion of a gas sample containing said first specific compound during a first interval of time and thereafter forming and analyzing a second portion of a gas sample containing said second specific compound during a second interval of time;

said forming and analyzing of the first portion comprising the steps of (a) flash-heating the vapor concentrator to a first temperature effective to remove volatile materials including said first specific compound from said vapor concentrator with said flow of carrier gas without removing said second specific compound, (b) gas chromatographically (GC)-separating said first portion in a gas chromatograph connected to said vapor concentrator, and (c) detecting said first specific compound in said GC-separated first portion;

said forming and analyzing of the second portion comprising the steps of (a) flash-heating the vapor concentrator to a second temperature higher than said first temperature to form said second portion, (b) gas chromatographically (GC)-separating said second portion, and (c) detecting said second specific compound in said GC-separated second portion.

2. A method as in claim 1 wherein said GC-separating steps include directing each of said portions of the gas sample into a first gas chromatograph and directing the effluent of said first gas chromatograph into a second gas chromatograph 3. A method as in claim 2 wherein said GC-separating steps include heating each of said gas chromatographs in accordance with predetermined heating schedules.

4. A method as in claim 3 wherein each of said heating schedules includes a substantially linear increase of temperature during said second interval of time to accelerate removal of separated vapors from each of said gas chromatographs substantially without decomposition of vapors of said specific compounds contained in said second portion of the gas sample.

5. A method as in claim 4 wherein each of said heating schedules includes, prior to GC-separating said second portion, heating each of said gas chromatographs to preset temperatures.

6. A method as in claim 2 wherein the sum of said first and second intervals of time is less than about thirty seconds.

7. A method as in claim 6 wherein the sum of said first and second intervals of time is less than about twenty seconds.

8. A method as in claim 1 wherein said detection steps (c) for said first portion and said second portion each comprises heating said respective portion under conditions sufficient to produce a specific gas from said vapors of said specific compounds and thereafter detecting the specific gas produced during said heating step.

9. A method as in claim 8 wherein said specific compounds are organic nitrogen-containing compounds and said specific gas is nitric oxide.

10. A method as in claim 9 wherein said detecting steps include generating detection signals from which the presence and identity of said specific compounds may be automatically determined.

11. A method as in claim 10 wherein said first specific compound is methamphetamine and said second compound is cocaine or heroin, and said heating steps include passing said first and second portions in a flow of carrier gas through a pyrolyzer to which oxygen is also supplied.

12. A method as in claim 10 wherein said specific compounds include methamphetamine, cocaine, and heroin, said flash-heating step to form said first portion of the gas sample is operable to remove vapors of methamphetamine from said vapor concentrator, and said flash-heating step to form said second portion of the gas sample is operable to remove vapors of cocaine and heroin from said vapor concentrator.

13. A method as in claim 1 wherein said GS-separating steps include directing each of said portions of the gas sample into a gas chromatograph and heating said gas chromatograph according to a predetermined heating schedule, said heating schedule including the steps of: (i) between the steps of GC-separating said first portion and flash-heating the vapor concentrator to said second temperature, heating said gas chromatograph to a third temperature, (ii) then maintaining said gas chromatograph at substantially said third temperature for a predetermined period of time, and (iii) then increasing the temperature of said gas chromatograph above said third temperature in a substantially linear fashion.

14. A method of rapidly and selectively detecting one or more of the compounds methamphetamine, cocaine, and heroin comprising:
  (a) directing air containing vapors of one or more of said compounds into a vapor concentrator so as to trap said vapors in said vapor concentrator;
  (b) while flowing a carrier gas through the vapor concentrator and through a gas chromatograph connected to said vapor concentrator, flash-heating said vapor concentrator to a first temperature effective to remove vapors of methamphetamine, if present, from said vapor concentrator substantially without removing vapors of cocaine or heroin from said vapor concentrator;
  (c) gas chromatographically (GC)-separating said vapors of methamphetamine, if present, from other materials removed from said vapor concentrator as a result of said flash-heating step;
  (d) analyzing the effluent of said gas chromatograph to detect methamphetamine, if present, in said effluent;
  (e) flash-heating said vapor concentrator to a second temperature to remove vapors of cocaine and heroin, if present, from said vapor concentrator;
  (f) GC-separating said vapors of cocaine and heroin, if present, from each other and from other materials removed from said vapor concentrator in said second flash-heating step; and
  (g) analyzing the effluent of said gas chromatograph to detect cocaine and heroin, if present, in said effluent.

15. A method as in claim 14 including, between steps (d) and (e), heating said gas chromatograph to a predetermined temperature.

16. A method as in claim 14 wherein steps (b) through (g) are performed in a total interval of time less than 30 seconds.

* * * * *